United States Patent [19]
Stock et al.

[11] Patent Number: 5,739,412
[45] Date of Patent: Apr. 14, 1998

[54] GAS SAMPLING SYSTEM HAVING A MOUTHPIECE

[75] Inventors: Burkhard Stock, Lübeck; Jürgen Sohège, Stockelsdorf, both of Germany

[73] Assignee: Drägerwerk Aktiengesellschaft, Lübeck, Germany

[21] Appl. No.: 759,921

[22] Filed: Dec. 4, 1996

[30]   Foreign Application Priority Data

Dec. 8, 1995 [DE] Germany ................... 195 45 794.3

[51] Int. Cl.$^6$ ..................... G01N 1/22; G01N 33/497
[52] U.S. Cl. ........................... 73/23.3; 73/863.61
[58] Field of Search ................. 73/23.3, 863.61,
  73/863.41, 864.81; 422/84; 436/900; 340/576;
  128/719; 180/272

[56]          References Cited

U.S. PATENT DOCUMENTS

| | | | |
|---|---|---|---|
| 4,677,987 | 7/1987 | Choksi | 422/84 X |
| 4,736,619 | 4/1988 | Legrand | 422/84 X |
| 5,111,827 | 5/1992 | Rantala | 128/719 |
| 5,143,695 | 9/1992 | Van Den Burg | 422/84 |
| 5,321,972 | 6/1994 | Stock | 422/84 X |

FOREIGN PATENT DOCUMENTS 2035982  1/1972  Germany.

Primary Examiner—Michael Brock
Attorney, Agent, or Firm—Walter Ottesen

[57]          ABSTRACT

The combination of the invention includes a mouthpiece 1 and a sample-taking system 8 for analyzing a gas sample. The mouthpiece 1 has a flow resistor 5 in the exhalation direction and a sample-taking connecting element 6 for the gas sample to be analyzed. The sample-taking system 8 has a pump and a through-flow measuring device 13. The pump pumps the sample gas flow from the sample-taking connecting element via a sample line 9 into a measuring chamber 15 of an analyzer 16. The combination is improved in such a manner that calibration is made possible with a calibrating gas flow greatly reduced compared to the flow of gas to be measured. This is achieved in that the sample-taking connecting element 6 is connected to the mouthpiece 1 forward of the flow resistor 5 viewed in the exhalation direction. The sample line 9 includes a flow throttle 11 in through-flow direction and an outlet opening 12 opening to the ambient. The through-flow measuring device 13 is connected to the sample line 9 forward of the flow throttle 11 as seen in the through-flow direction. The pump 14 takes the gas sample between the flow throttle 11 and the outlet opening 12.

7 Claims, 1 Drawing Sheet

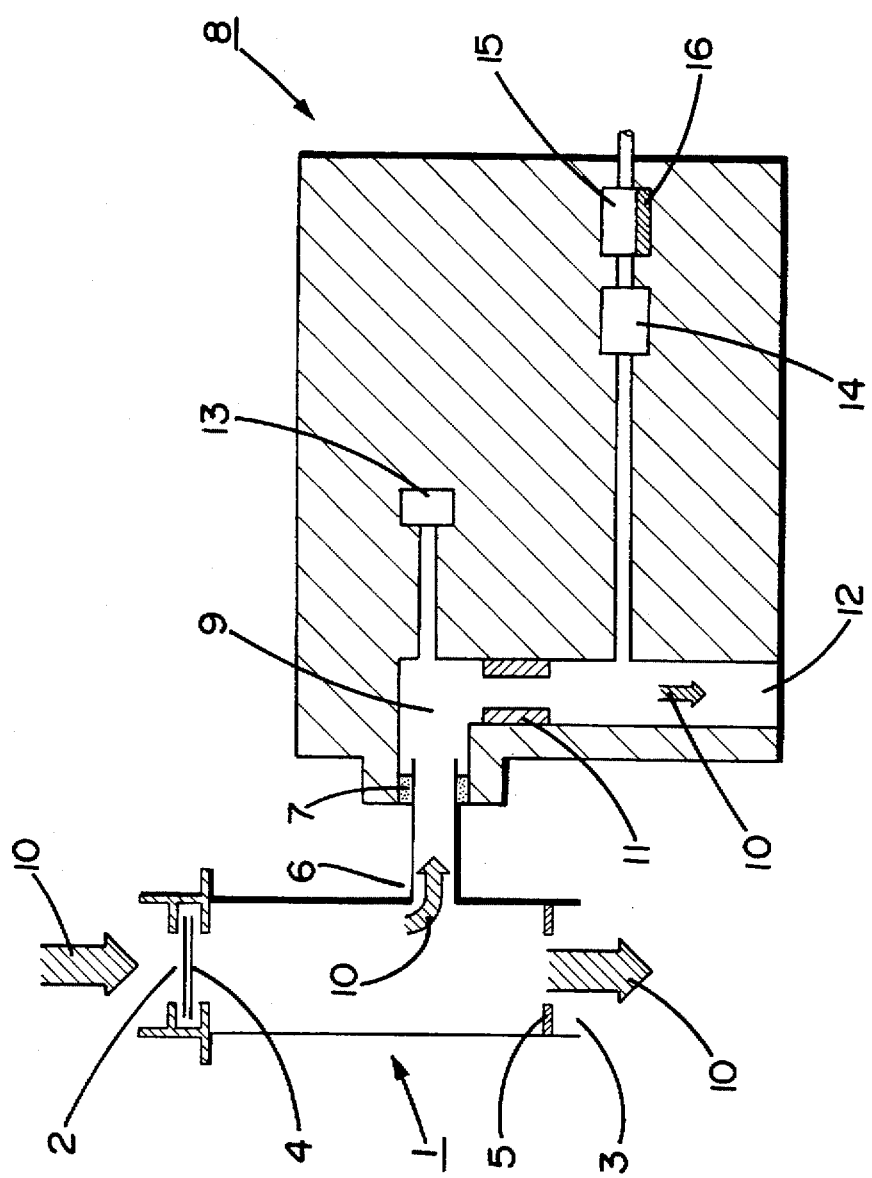

GAS SAMPLING SYSTEM HAVING A MOUTHPIECE

BACKGROUND OF THE INVENTION

German patent publication 2,035,982 discloses an arrangement for analyzing respiratory gas including a breathing tube as a mouthpiece. The arrangement also includes the following: a measurement diaphragm located in the respiratory tube, a pump for pumping a gas sample out of the respiratory tube and a gas analyzer for analyzing the gas sample. In this arrangement, the test person blows into the respiratory tube. During the expiration phases, this known arrangement performs the following: takes a gas sample from the respiratory gas, conducts the gas sample to a gas analyzer and determines the oxygen absorption of the test person from the measured oxygen concentration and from the expiration volume. The calibration of an arrangement of this kind generally presents few difficulties because oxygen/air mixtures having a defined oxygen component are simple to produce and are available in sufficient quantity.

If the above-mentioned arrangement is utilized to measure other components of the respiratory gas instead of oxygen, such as determining breath alcohol, the calibration becomes more difficult because calibration systems primarily operate at a low gas flow between approximately 6 L/min and 9 L/min. The difficulty in calibration is that the measurement diaphragm of the exhalation tube and the through-flow measuring system, which is connected to the measurement diaphragm, are dimensioned for high gas flows between 25 L/min and 50 L/min. If the known arrangement is charged with a low gas flow for calibration, then the through-flow measuring system detects no clear signal. The diameter of the measurement diaphragm could be reduced in order to improve the signal/noise ratio; however, the exhalation resistance then increases and is then too high for the normal operation.

SUMMARY OF THE INVENTION

It is an object of the invention to improve an arrangement of the kind described above so that a calibration of the arrangement is made possible with a calibration gas flow which is greatly reduced compared to the measurement gas flow.

The combination of the invention includes a mouthpiece and a system for taking and analyzing a sample of respiratory gas. The mouthpiece includes: an inlet opening into which a test person exhales the respiratory gas; an outlet opening; a channel between the openings along which the respiratory gas flows; a flow resistor mounted in the channel downstream of the inlet opening. The combination further includes: a connecting element communicating with the channel for receiving a sample of the respiratory gas; the connecting element being connected into the channel upstream of the flow resistor as viewed in the flow direction of the exhaled respiratory gas; the system including a sample line having a first end connected to the connecting element and a second end opening to the ambient; the sample line having a flow throttle mounted therein; through-flow measuring means for measuring the through flow of the sample passing through the sample line and the through-flow measuring means being connected into the sample line upstream of the flow throttle; the system including an analyzer defining a measuring chamber; pumping means for drawing the sample from the connecting element through the sample line and into the measuring chamber; and, the pumping means being connected into the sample line between the flow resistor and the second end of the sample line.

In the combination of the invention, the gas flow is subdivided within the mouthpiece into a main gas flow, which flows directly to the ambient, and a gas flow to be measured, which is conducted through the sample-taking system and is adjusted as to the through-flow volume to a value which is supplied by known calibration devices. The advantage of the invention is seen in that a calibration of the sample taking system is possible under realistic through-flow conditions. Because the gas sample for the gas analysis is taken in flow direction rearward of a flow throttle within the sample-taking line, the gas analysis is carried out under ambient pressure conditions without being affected by pressure fluctuations within the mouthpiece which perforce occur during exhalation.

The respective through-flow cross sections of the flow resistance and the flow throttle are advantageously dimensioned so that approximately one quarter of the gas flow exhaled via the mouthpiece is conducted through the sample-taking connection. The gas flow within the sample-taking line of the system is advantageously between 4 L/min and 12 L/min.

The sample-taking connection or connecting element of the mouthpiece is connected via a detachable coupling to the sample-taking system. In this way, for calibration, the mouthpiece is removed from the sample-taking system and a calibrating flow is fed directly into the sample-taking line.

The mouthpiece is advantageously provided with a check valve to prevent a back flow of respiratory gas.

The combination of the invention is especially suitable for analyzing the component of alcohol in respiratory gas.

BRIEF DESCRIPTION OF THE DRAWINGS

The invention will now be described with respect to the single FIGURE of the drawing which is a schematic of the combination according to the invention for taking samples of respiratory gas.

DESCRIPTION OF THE PREFERRED EMBODIMENTS OF THE INVENTION

Referring to the drawing, a mouthpiece 1 includes: a blow-in opening 2, a blow-out opening 3, a check valve 4 in the vicinity of the blow-in opening 2 and a flow throttle 5 at the elevation of the blow-out opening 3. A sample-taking connection 6 branches off between the check valve 4 and the flow throttle 5. The sample-taking connection 6 is attached in an insert coupling 7 of a sample-taking system 8 and establishes the flow connection to a sample-taking line 9 of the system 8. The blow direction through the mouthpiece 1 and through the system 8 takes place in the direction of arrow 10.

The respiratory gas flows in via the connection 6 into the line 9 within the system 8. The respiratory gas flows via a flow throttle 11 to an outlet opening 12 and can there flow into the ambient. A pressure sensor 13 is provided between the insert coupling 7 and the flow throttle 11 and functions as a through-flow measuring device. The pressure sensor 13 is connected to the line 9. The gas sample to be analyzed is pumped by a pump 14 (located directly downstream of the flow throttle 11) into a measuring chamber 15 of an electrochemical measuring cell 16. By taking the gas sample rearward of the flow throttle 11, the gas to be measured is conducted at atmospheric conditions into the measuring chamber 15 and is there electrochemically converted so that only ambient pressure fluctuations but not fluctuations as a consequence of exhaling through the mouthpiece 1 must be considered for making pressure corrections in an evaluation unit (not shown).

The gas flow through the sample-taking line 9 is, in a manner known per se, measured via the dynamic pressure, which builds up forward of the flow throttle 11, utilizing the pressure sensor 13. The flow resistor 5 and the flow throttle 11 are dimensioned with respect to their respective cross sections so that approximately three quarters of the exhaled gas flows off via the flow resistor 5 and approximately one quarter flows off to the ambient via the flow throttle 11.

If the test persons blows, for example, at a gas flow of approximately 25 L/min into the mouthpiece 1, then the flow distribution between the flow resistor 5 and the flow throttle 11 is approximately 19 L/min for the flow resistor 5 and 6 L/min for the flow throttle 11.

The advantage of the combination of the invention is that, because of the flow division between the mouthpiece and the sample-taking system 8, a known calibration device (not shown) can be connected directly to the insert coupling 7 thereby making possible a calibration under realistic exhalation conditions. The calibration device can be adjusted to gas flows between approximately 6 L/min and 9 L/min.

The pressure sensor 13 is required for detecting a minimum through-flow within the line 9. The pressure sensor 13 can be operated with the same response thresholds during exhalation via the mouthpiece 1 as well as during calibration via the insert coupling 7. This significantly simplifies the manipulation of the combination according to the invention.

It is understood that the foregoing description is that of the preferred embodiments of the invention and that various changes and modifications may be made thereto without departing from the spirit and scope of the invention as defined in the appended claims.

What is claimed is:

1. The combination of a mouthpiece and a system for taking and analyzing a sample of respiratory gas, the combination comprising:

said mouthpiece including: an inlet opening into which a test person exhales the respiratory gas; an outlet opening; a channel between said openings along which said respiratory gas flows; a flow resistor mounted in said channel downstream of said inlet opening; and, a connecting element communicating with said channel for receiving a sample of said respiratory gas;

said connecting element being connected into said channel upstream of said flow resistor as viewed in the flow direction of the exhaled respiratory gas;

said system including a sample line having a first end connected to said connecting element and a second end opening to the ambient;

said sample line having a flow throttle mounted therein;

through-flow measuring means for measuring the through flow of said sample passing through said sample line and said through-flow measuring means being connected into said sample line upstream of said flow throttle;

said system including an analyzer defining a measuring chamber;

pumping means for drawing said sample from said connecting element through said sample line and into said measuring chamber; and, said pumping means being connected into said sample line between said flow throttle and said second end of said sample line.

2. The combination of claim 1, said flow resistor and said flow throttle having first and second cross sections which are so dimensioned that approximately a quarter of the flow of the exhaled respiratory gas passes through said connecting element.

3. The arrangement of claim 1, said flow resistor and said flow throttle having first and second cross sections which are so dimensioned that the gas flow of said sample in said sample line is between 4 Liters/minute and 12 Liters/minute.

4. The arrangement of claim 1, said system including a releasable coupling for coupling said system to said connecting element.

5. The arrangement of claim 1, said mouthpiece further including a check valve.

6. The arrangement of claim 4, said coupling being adapted to be connected to a calibrating gas source.

7. The arrangement of claim 1, wherein said measuring chamber includes a measuring cell for measuring the portion of alcohol in said sample of respiratory gas.

* * * * *